(12) United States Patent
Boldt

(10) Patent No.: US 12,563,351 B2
(45) Date of Patent: *Feb. 24, 2026

(54) HEARING DEVICE COMPRISING A STRESS EVALUATOR

(71) Applicant: GN Hearing A/S, Ballerup (DK)

(72) Inventor: Jesper Bünsow Boldt, Måløv (DK)

(73) Assignee: GN HEARING A/S, Ballerup (DK)

( * ) Notice: Subject to any disclaimer, the term of this patent is extended or adjusted under 35 U.S.C. 154(b) by 86 days.

This patent is subject to a terminal disclaimer.

(21) Appl. No.: 17/740,299

(22) Filed: May 9, 2022

(65) Prior Publication Data

US 2022/0272465 A1     Aug. 25, 2022

Related U.S. Application Data

(63) Continuation of application No. PCT/EP2020/084843, filed on Dec. 7, 2020.

(30) Foreign Application Priority Data

Dec. 20, 2019     (EP) ..................................... 19218513

(51) Int. Cl.
H04R 25/00 (2006.01)
A61B 5/00 (2006.01)
(Continued)

(52) U.S. Cl.
CPC ....... H04R 25/505 (2013.01); A61B 5/02055 (2013.01); A61B 5/165 (2013.01);
(Continued)

(58) Field of Classification Search
CPC .. H04R 25/505; H04R 25/554; H04R 25/604; H04R 2225/39; H04R 2225/41;
(Continued)

(56) References Cited

U.S. PATENT DOCUMENTS

2007/0071262 A1* 3/2007 Rass ...................... H04R 25/70
                                                              381/309
2014/0369537 A1 12/2014 Pontoppidan et al.
                       (Continued)

FOREIGN PATENT DOCUMENTS

CN          101783998          7/2010
CN          103239236          8/2013
                  (Continued)

OTHER PUBLICATIONS

PCT International Search Report and Written Opinion for International Appln. No. PCT/EP2020/084812 dated Feb. 19, 2021.
(Continued)

*Primary Examiner* — Norman Yu
(74) *Attorney, Agent, or Firm* — Vista IP Law Group, LLP

(57) ABSTRACT

A hearing device configured to be worn by a user comprises one or more microphones, a processing unit, a speaker, a wireless communication unit, and stress evaluator. The user wearing the hearing device is in an environment defined by an acoustic scene. The microphones receive audio signals from audio sources in the environment and provide them to the processing unit which applies processing parameters to thereby process the audio signals. The speaker provides the processed audio signals to the user. The stress evaluator generates an indication of stress of the user, stress of the user being related to the acoustic scene. The processing unit then decides whether to perform an action on the basis of the received audio signals and the indication of stress of the user.

33 Claims, 7 Drawing Sheets

(51) Int. Cl.

| | |
|---|---|
| *A61B 5/0205* | (2006.01) |
| *A61B 5/16* | (2006.01) |
| *G10L 25/63* | (2013.01) |
| *A61B 5/024* | (2006.01) |
| *A61B 5/0531* | (2021.01) |

(52) U.S. Cl.

CPC ............ *A61B 5/6817* (2013.01); *G10L 25/63* (2013.01); *H04R 25/554* (2013.01); *H04R 25/604* (2013.01); *A61B 5/02438* (2013.01); *A61B 5/0531* (2013.01); *H04R 2225/39* (2013.01); *H04R 2225/41* (2013.01); *H04R 2225/55* (2013.01)

(58) Field of Classification Search

CPC . H04R 2225/55; A61B 5/02055; A61B 5/165; A61B 5/6817; A61B 5/02438; A61B 5/0531; G10L 25/63

USPC ...................................... 381/312, 315, 58, 56

See application file for complete search history.

(56) References Cited

U.S. PATENT DOCUMENTS

| | | | |
|---|---|---|---|
| 2017/0071551 A1* | 3/2017 | Jain ....................... | A61B 5/4884 |
| 2017/0112671 A1 | 4/2017 | Goldstein | |
| 2017/0289704 A1* | 10/2017 | Frederiksen ........... | G16H 40/63 |
| 2019/0149927 A1 | 5/2019 | Zhang et al. | |
| 2019/0253793 A1* | 8/2019 | Pedersen ................ | H04R 25/60 |
| 2020/0120433 A1* | 4/2020 | Serman ................ | H04R 25/558 |
| 2020/0268265 A1 | 8/2020 | Walsh et al. | |

FOREIGN PATENT DOCUMENTS

| | | | |
|---|---|---|---|
| CN | 107801138 | | 3/2018 |
| CN | 110062318 | | 7/2019 |
| DE | 102009043775 | * | 4/2011 |
| DE | 102018204695 | | 12/2018 |
| EP | 3618456 | | 3/2020 |
| WO | WO 2011/038767 | | 4/2011 |
| WO | WO 2012/072141 | | 6/2012 |

OTHER PUBLICATIONS

Extended European Search Report for EP Patent Appln. No. EP19218516.3 dated Jun. 5, 2020.

PCT International Search Report and Written Opinion for International Appln. No. PCT/EP2020/084843 dated Feb. 11, 2021.

Extended European Search Report for EP Patent Appln. No. EP19218513.0 dated Mar. 19, 2020.

Foreign Chinese office action dated Jun. 14, 2024 for Chinese Patent Application No. 202080087626.4.

Foreign Chinese office action dated Jul. 21, 2024 for Chinese Patent Application No. 202080087211.7.

Non-Final Office Action for U.S. Appl. No. 17/738,618 dated Jul. 22, 2024.

Foreign Office Action for Chinese Patent Application No. 202080087211.7 dated Jan. 18, 2025.

Final Office Action for U.S. Appl. No. 17/738,618 dated Dec. 6, 2024.

Notice of Allowance for U.S. Appl. No. 17/738,618 dated Mar. 21, 2025.

* cited by examiner a)

Complexity of acoustic scene b)

Complexity of acoustic scene

HEARING DEVICE COMPRISING A STRESS EVALUATOR

RELATED APPLICATION DATA

This application is a continuation of International Patent Application No. PCT/EP2020/084843 filed on Dec. 7, 2020, which claims priority to, and the benefit of, European Patent Application No. 19218513.0 filed on Dec. 20, 2019. The entire disclosures of the above applications are expressly incorporated by reference herein.

FIELD

The present disclosure relates to a hearing device configured to be worn by a user and comprising a stress evaluator which generates an indication of stress of the user. The hearing device is configured to decide whether to perform an action depending on the indication of stress of the user.

BACKGROUND

Stress is the most common risk factor for a large variety of mental and physical diseases and health problems. Stress is associated with increased risk for cardio-vascular diseases, cancer, chronic pain, anxiety, depression, etc. Given these effects of stress on health, numerous techniques and methods have been applied to assess stress of an individual and/or population. The most used methods for assessing stress of an individual are conducting stress interviews and questionnaires and measuring biological processes regulated by stress exposure. However, most of the methods often lack details about origin of stress and cannot be performed in a real time and real life scenarios.

With the development of new technologies and personal devices, it is believed that in the future many people will perform daily activities while wearing a hearing device or hearable. One of the uses of hearing devices or hearables in the future may be stress assessment and stress relief.

SUMMARY

It is an object to provide a hearing device which can determine stress of the hearing device user.

It is a further object to provide a hearing device which can reduce stress of the hearing device user.

It is a yet further object to provide a hearing device which can identify hearing problems of the hearing device user.

Disclosed, in a first aspect, is a hearing device configured to be worn by a user. The hearing device comprises one or more microphones, a processing unit, a speaker, a wireless communication unit, and a stress evaluator. The user wearing the hearing device is in an environment. The environment is defined by an acoustic scene. The one or more microphones are configured to receive audio signals from audio sources in the environment and provide the audio signals to the processing unit. The processing unit is configured to apply processing parameters to thereby process the audio signals. The speaker is configured to provide the processed audio signals to the user. The stress evaluator is configured to generate an indication of stress of the user. The stress of the user being related to the acoustic scene. The processing unit is configured to decide whether to perform an action. The decision on whether to perform the action is based on the received audio signals and the indication of stress of the user.

The hearing device may be an electronic device designed for multiple purposes ranging from wireless transmission to communication objectives, medical monitoring, fitness tracking, etc. The hearing device may be a hearing aid, headset, headphones, earphones, noise cancelling headset, hearable, cochlear implant, and the like. A user of the hearing device may be a person with normal hearing or it may be a person with any kind of hearing problems.

The hearing device comprises one or more microphones. The microphone(s) typically convert sounds from the environment into corresponding electrical signals. The one or more microphones may be arranged outside of the user's ear or they may be arranged inside the user's ear. The microphone(s) arranged outside of the user's ear or in the ear but facing the user's surroundings may receive sounds from the surroundings as well as the user's spoken voice. The microphone(s) arranged inside the ear canal may receive vibrations of the user's bone structures which occur when the user speaks. The received signal is then processed and may further be provided to the user via a speaker. The one or more microphones may include a boom microphone and/or an in-the-ear-microphone. The in-the-ear microphone may be measuring vibrations generated when the user speaks.

The one or more microphones are configured to receive audio signals from audio sources in the environment. The audio signals are a representation of sound having frequencies in the audio frequency range from around 20 Hz up to around 20 KHz. The audio signals may be a voice of a person talking to the user of the hearing device or voices from a group of people, and/or audio content from an external device, e.g. music. The audio signals may be noise from the user's surroundings, etc.

The audio sources may be people talking, speakers playing music, sounds from traffic, noise from people's activities on the street, etc. The user wearing the hearing device is present or situated in an environment. The environments may be of different types, such as an office space, nature, street, user's home, museum, shopping mall, airport, etc. The environment is defined by an acoustic scene. The environment may also be defined by visual signals and visual arrangement of objects within the scene.

The acoustic scene may be characterized by a number of audio sources, their sound level, and their arrangement, geometry of a room, such as the area of the floor, the height of the walls, the number of people in the room/scene, reverberation, music, etc. The acoustic scene may also be characterized by a scenario of an event, such as a meeting, a cocktail party, a discussion in an office space, a discussion with a cashier, etc.

The audio signals are converted in the one or more microphones and provided to the processing unit. The one or more microphones and processing unit may be connected via electronic conducting lines configured to conduct electrical signals from the microphones to the processing unit.

The hearing device comprises the processing unit. The processing unit may comprise a number of electronic components such as filters and amplifiers which may then modify the electrical signals received from the one or more microphones. The received electrical signals may be amplified by the processing unit. The processing unit may filter out any noise present in the sound received by the hearing aid and output clear and undistorted electric signals which the user wants to hear.

The processing unit is configured to apply processing parameters to thereby process the audio signals. The processing parameters may include amplification, attenuation, filtering, compression, echo management, speech recognition, noise cancellation, equalization, source separation and classification, beamforming and directionality of sounds, feedback cancellation, etc. The processing parameters may be adjusted by the user and/or may be adjusted automatically. The adjustment of the processing parameters may depend on the user's environment, the acoustic scene, and the audio signals received by the hearing device. The processing parameters may also depend on the user's hearing.

The hearing device comprises a speaker, such as a loudspeaker, receiver or output transducer. The speaker may be in a direct communication with the processing unit via electric conducting lines thereby receiving the audio signals processed by the processing unit. The speaker converts the processed audio signals which are in electronic form into sound. The speaker is configured to provide the processed audio signals to the user, in the form of sound.

The hearing device further comprises a wireless communication unit. The wireless communication unit may provide wireless connection between the hearing device and an external device. The external device may be the user's smart phone, laptop, tablet, or similar. In the case of the hearing device being a hearing aid for binaural hearing, the wireless communication unit may provide communication between the left and right hearing aid. The hearing device may communicate with computers being part of a cloud or server via the wireless communication unit. The wireless communication unit may receive signals which are used for providing sound to the user via the speaker.

The hearing device comprises a stress evaluator. The stress evaluator may comprise one or more sensors which measure one or more parameters related to the user's physiological condition and a processor configured to compile the received sensor measurements. The processor may have pre-programmed algorithms for determining a cognitive load of the user. The stress evaluator may be configured to perform various physiological measurements, such as electroencephalogram (EEG), electrocardiogram (ECG), electrooculography (EOG), temperature, skin resistance, skin conductance, beat rate, respiratory rate, blood volume pulse, electrodermal activity (EDA), etc., which are directly linked to stress of the user. The stress evaluator is configured to generate an indication of stress of the user. The generated indication of stress may be based on the performed physiological measurements and/or parameters obtained by the one or more sensors.

In the present context, stress of the user may be related to the user's hearing capabilities, such as in a specific acoustic scene of a specific environment. If the user already has a hearing loss, stress of the user may occur if the hearing device does not sufficiently account for the user's hearing loss. This may be due to incorrect settings in the hearing device, incorrect mode, if the user's hearing loss has changed etc. If the user is not a hearing device user, and the user does not yet have a detected hearing loss, stress of the user may occur if a hearing loss of the user has developed. Stress of the user may also relate to the current signal processing in the hearing device, i.e. to the processing parameters.

In the present context, the term "stress" is to be interpreted as a load on the user and the user's subjective perception and understanding of the acoustic scene. It may also be interpreted as cognitive load, i.e. the degree of concentration required for the user to correctly understand current or present audio signals. When the acoustic scene reaches a certain level of complexity, the user may unconsciously adapt/use his/her abilities to meet the challenge.

When the acoustic scene is considered by the user as exceeding the available abilities and resources, stress would appear. Stress may refer to perceptually induced variations on the production of speech. Stress may refer to increased pulse, heart rate, and variations thereof. Stress may refer to changes in body temperature. Stress may refer to changes in skin resistance of the user, a galvanic skin response, and/or a skin conductance response. Stress may relate only to the usage of the hearing device and the user's experience of the hearing device. For instance, stress of the user may be increased if the hearing device does not appropriately compensate for the user's hearing deficit. It is an advantage that the hearing device according to the present disclosure can apply specific signal processing in order to compensate for stress of the user or to decrease stress level.

The indication of stress is to be interpreted as a stress quantifier, i.e. as a parameter which describes a level of stress of the user. The indication of stress may be compared with a threshold stress value in order to determine whether the user is stressed or not. The indication of stress in various acoustic scenes may be used in a feedback-loop where gain and directionality in the hearing device is adjusted continuously. If a positive result is obtained, i.e. the indication of stress drops, then the adjustment was correct and further adjustments in the same direction may be applied. If the indication of stress raises, the adjustment may be rolled back and/or other adjustments may be introduced.

Stress of the user is related to the acoustic scene. The more complex the acoustic scene is, the more stress it may cause in the user, as the user may be deconcentrated by many factors present in the acoustic scene. Namely, a complex acoustic scene puts a high cognitive demand on the user. The complex acoustic scene may comprise more than one audio source. However, the same acoustic scene may be perceived differently by different users, depending on the users' hearing. Additionally, the same acoustic scene may be perceived differently by the same user at two different points in time depending on the user's mood and/or the user's progressing hearing deficit. The relation between the acoustic scene and stress originates from an, e.g. unconscious, acoustic scene analysis performed by the user. The user being in an acoustic scene may want to identify arrangement and classification of audio sources and acoustic events, their possible motion (e.g. a person walking, a train accelerating, etc.), speaker identification, etc. The more details about the acoustic scene which are to be identified, the more complex, and demanding for the user it is.

The processing unit is configured to decide whether to perform an action. In cases when stress of the user is below a predefined threshold, the decision of the processing unit of whether to perform the action may be a decision not to perform any action. In cases when stress is equal or above the predefined threshold, and/or when the acoustic scene changes, the decision of the processing unit of whether to perform an action may be a decision to perform an action, such as the action of adjusting the processing parameters of the processing unit. Alternatively, the decision may be a "delta-decision", i.e. based on changes in the indication of stress over time or a sudden change even though the indication of stress is not over a certain threshold. The decision may also be based on a relative indication of stress, e.g. what is the current indication of stress relative to an average of the specific user. The action may be a change in the processing parameters, a notification to the user, and/or sending the indication of stress to an external device, e.g. the user's phone, cloud, server, database. The action may be to make a data point as input for future decisions in the hearing device, e.g. to perform different processing next time, or only change the processing parameters after a number of similar observations.

The decision on whether to perform the action is based on the received audio signals and the indication of stress of the user. The received audio signals may be analysed by the processing unit to thereby reconstruct the objective acoustic scene, at least partly. The indication of stress is also related to the acoustic scene as perceived by the user, i.e. the subjective acoustic scene. When making the decision, the processing unit may compare the subjective acoustic scene perceived by the user and the objective acoustic scene. In some cases, the acoustic scene may objectively be complex, e.g. a background noise is extremely high, and therefore stress of the user may be reasonable and expected. In these scenarios, the processing unit may perform no action automatically.

Assessing hearing capabilities and abilities of the user of the hearing device is important in providing the best user experience. An increase in average stress level on a monthly time-scale not explained by more complex acoustic environments or increasing hearing loss could be caused by more severe health issues, e.g. cognitive decline (dementia), insomnia, or other physiological problems. The hearing device as disclosed provides optimal settings and adjustments for a particular user being in a particular environment. Furthermore, the hearing device of the present disclosure can provide information and indications of hidden hearing loss of the user, and/or more severe health issues, such as dementia, insomnia, etc. Having information about hearing deficit and/or uncompensated hearing loss it is possible to timely resolve the issue and thereby improve the user's everyday life.

In some embodiments, the stress evaluator may comprise a temperature sensor, a heart rate sensor, a skin resistance sensor, and/or the one or more microphones. The stress evaluator may also comprise an electrodermal activity sensor for measuring changes in skin conductance resulting from the sympathetic nervous system activity and being one of stress indicators. The stress evaluator may further comprise a respiratory rate sensor. The sensors may be arranged on the outside of the hearing device to thereby be in a direct contact with the user's skin and measure temperature, skin resistance, and/or heart rate of the user. Skin conductance response measured by the skin resistance sensor is a measure that is traditionally associated with workload and especially with arousal states accompanied by mental effort and emotions. Higher workload normally yields higher number of skin conductance responses. Heart rate normally increases when the user is stressed. Temperature of different body parts may be different when the user is exposed to stress. Assessing stress using body temperature, heart rate, skin resistance, and/or speech is inexpensive and non-intrusive, as all these parameters can be obtained without the user noticing it. Furthermore, having multiple and different sensors to perform measurements which are used in determination of the indication of stress, the accuracy of the determination is improved. By combining a plurality of uncorrelated sensors, the confidence of the determined indication of stress in increased, as multiple sensors may provide more reliable data than a single one.

In some embodiments, the indication of stress may be generated based on at least the user's speech detected by the one or more microphones. The user's speech may be detected by a boom microphone arranged close to the user's mouth. The user's speech may be detected by a microphone arranged in or at the hearing device, such as a microphone behind the ear, and/or in the ear, such as at the concha of the ear or in the ear canal etc. The processing unit may then isolate the speech from other sounds picked up by the microphone and analyse it further. Stressed speech may be defined as the speech produced under any condition that causes the speaker to vary speech production from neutral condition. The speech may be affected by the mental state of the speaker/user and can thus be used for generation of the indication of stress. The speech may be analysed by analysing various parameters such as a speech speed, speech length, time limitation, tempo, pitch, content of speech, fundamental frequency and formants, stuttering, etc. For instance, in the low stress conditions, the user normally speaks calmly using a clear voice with normal speed, conversation/talking is not urged to speed up its performance. The processing unit may then generate the indication of stress which corresponds to acoustic scenes where the user has no stress. In the high stress conditions (e.g. presence of white noise, ambulance sound, etc.), the user may talk fast, using short sentences and an urgent tone, make mistakes and repeat some of the words, etc. The processing unit may generate the indication of stress which corresponds to acoustic scenes where the user feels stressed. When the processing unit generates the indication of stress which shows that the user is stressed, received audio signals from the environment will be analysed in order to make a decision whether to perform an action or not. It is advantageous to determine the indication of stress based on the user's speech as the speech is affected by the environmental conditions. Therefore, it is possible to determine if the user is stressed due to, e.g. exposure to high noises or simply because the user has a hearing deficit which is not compensated for. Furthermore, by identifying stress by analysing the user's speech detected by the one or more microphones, complexity of the hearing device is reduced as the microphones which are already a part of the hearing device are used for another purpose, i.e. for the user's speech analysis and there is no need for additional sensors for stress detection.

When comparing two speech signals and their spectrograms, one uttered with neutral emotion and the other with anger emotion it is possible to identify some visible differences especially in terms of signal duration and amplitude. The speech uttered with anger emotion may have a duration less than that uttered with neutral emotion. The average amplitude of the signal may have a higher value in case of the speech signal uttered with anger emotion. The spectrograms may show that the frequencies have shifted upward or have higher values in the speech signal uttered with anger emotion compared to the speech uttered with neutral emotion.

In some embodiments, the action may comprise adjusting the processing parameters based on the decision. The processing parameters may continuously be adjusted based on updated decisions. By adjusting the processing parameters based on the decision, user's stress can be reduced. For instance, for the wearer of the hearing device, e.g. headphones, the indication of stress can be used for performing the action of automatic volume amplification or volume decrease. Alternatively, the action may be a suggestion to the wearer to increase/decrease the volume of the sound. In another example, for the wearer of the hearing device such as a hearing aid, the indication of stress can be used for performing the action of mode switching. Alternatively, the action may be a suggestion to the wearer to use other operational modes or settings in the hearing aid, to get more amplification, to visit a healthcare professional, or to provide suggestion on how to optimize the current situation. Changing the mode or adjusting setting of the hearing device may optimize sound processing in the hearing device and thereby reduce stress of the user and/or improve hearing.

In some embodiments, the processing parameters may comprise a first processing parameter and a second processing parameter. The processing unit may then be configured for changing from the first processing parameter to the second processing parameter based on a detection that the acoustic scene changes from a first acoustic scene to a second acoustic scene. The processing unit may reconstruct the acoustic scene based on the received audio signals. The first acoustic scene may be an acoustic scene with no or very little noise, such as user's home. The second acoustic scene may be an acoustic scene characterized with a high level of noise, such as busy street. If the user relocate from home to the busy street, the processing unit may, based on the detected noise level, apply noise cancellation to the received audio signal. This change in processing parameters may be applied even before the processing unit generates the indication of stress and thereby help the user not to feel stressed when changing the acoustic scene. Namely, the change of the processing parameters based on the change of the acoustic scene may prevent the user's stress. The change may also be based on the indication of stress, received audio signals, user's input, or some other parameter. The change in the processing parameters, may be changed either before or after the indication of stress is generated.

In some embodiments, the action may comprise providing a request to the user to adjust the processing parameters based on the decision. The hearing device may communicate with, e.g. the user's phone and send a message to the phone about the request. The user may decide whether to fulfil the request by switching between different operational modes. Sending the request may be the action performed by the processing unit. The request may be for instance a suggestion to the user to change/use different listening features. By sending the request to the user to adjust the processing parameters the user has a freedom to decide whether to make changes in the processing parameters or not. This improves user experience of the hearing device.

In some embodiments, the hearing device may further be configured for forwarding the user's speech to an external device. The external device may then perform processing of the user's speech. The external device may be the user's phone, a server in a cloud, or another electronic device. Speech processing may be highly demanding in terms of processing power. By forwarding the user's speech to the external device demands on the processing unit of the hearing device are relaxed.

In some embodiments, the hearing device may be communicatively coupled to a database comprising historical data. The historical data may relate to the user's perceptual hearing and/or a general perceptual hearing. The indication of stress may be generated based on the historical data. In the determination of the indication of stress, the historical data may be used in addition to the measurements obtained by the stress evaluator. Namely, the indication of stress may be determined based on a difference between the measurements obtained by the stress evaluator and one or more expected stress parameters. The expected stress parameters may form part of the historical data. Perceptual hearing includes both detecting a sound wave with the ear of a listener and interpretation of the detected sound signal by the brain of the listener. The general perceptual hearing relates to an average perceptual hearing which may be based on perceptual hearing of a plurality of listeners. Perceptual hearing may be defined for a specific environments and acoustic scenes.

The database may be an external database. The hearing device may get the historical data from the external database, and then use the data for generation of the indication of stress. Alternatively, the database may be a part of the hearing device itself in a form of a memory. The historical data may relate to the user's perceptual hearing in similar situations, i.e. in similar environments defined by similar acoustic scene and/or to perceptual hearing of other users of hearing devices. The historical data may contain indications of stress of a hearing device user and information about the environment. The historical data related to the user may also be used to determine changes in the user's hearing in long term, i.e. if the hearing has improved/degraded/changed in any way. A part of the historical data may be a comparison between a current stress measurement and another measurement from another point of time for similar environment. The user may often be in the same or similar situations. If the assessment of stress changes over time in situations of comparable complexity, the assessment of stress over time may provide an indication of progressing hearing deficit. Additionally, the historical data may comprise perceptual hearing of, e.g., 100 hearing device users being in the same environment with a similar acoustic scene. These data may then be compared with the generated indication of stress of the user being in the same environment. If the comparison reveals that the user's stress is different from the historical data of other users, it may be a sign of potential hearing problems of the user. In other words, through a population of hearing device users, an average perceptual hearing for acoustic scenes with different complexity could be obtained. This average could be used as a reference for the current user in the current situation. If the user is a long-term user, the historical data may comprise individual data of this particular user. For new users, the historical data may be based on general data, i.e. data from other users with a similar profile (defined by age, hearing deficit, etc.).

In some embodiments, the processing unit may be configured to detect a hearing deficit of the user, and/or an uncompensated hearing loss of the user, and/or a change in the hearing capability. The historical data may define one or more expected stress parameters. The expected stress parameters may be relative to the complexity of the acoustic scene. If one or more expected stress parameters comprise expected stress level parameter, by determining the difference (d) between the actual stress level (actual stress) and the expected stress level (expected stress) it can be determined whether the user is challenged or not. The user is challenged if the difference between actual and expected stress is above zero. The challenge may indicate uncompensated hearing loss and/or deficit, i.e. if $$d = \text{actual stress} - \text{expected stress}$$

is above zero, the processing unit may report uncompensated hearing loss of the user. Such difference may be tracked over a predetermined time span in order to calculate an average value of the difference. The predetermined time span may be one or more weeks, one or more months, or one year. The average value may provide a more accurate estimate on the hearing loss or deficit. The hearing deficit and/or the uncompensated loss of the user may be detected by comparing the received audio signals and the indication of stress of the user. The received audio signals may be a voice of a person talking to the user. The indication of stress may be determined based on the user's speech. The processing unit may compare the content of the person's speech with the content of the user's speech. If the user's speech does not correspond to the speech of the person, it may be a sign of hearing problems of the user. By detecting the hearing problems, the user may be alerted on time and without going to a doctor about the problems. Prevention of further problems may also be achieved.

In some embodiments, the hearing deficit and/or the uncompensated hearing loss of the user and/or the change in the hearing capability may be detected based on the acoustic scene and the indication of stress. The processing unit may restore details about the objective acoustic scene from the received audio signals. Based on the objective acoustic scene the processing unit may predict the user's stress in the given situation. If this prediction does not match the indication of stress generated by the evaluation means with the prediction of the processing unit, it may be a sign of the hearing deficit and/or hearing loss of the user. Furthermore, the processing unit may predict the user's stress based on previous indications of stress generated in similar situations. Machine learning algorithms may be used for predicting the user's behaviour in particular situations and thereby detect change in the hearing capability of the user. Additionally or alternatively, the processing unit may use historical data stored in the database in detection of the hearing problems of the user. By detecting the hearing problems based on the acoustic scene and the indication of stress particulars about the problems can be identified, such as if the user has a problem of hearing sounds coming from behind the user, or in hearing low frequency sounds, etc.

In some embodiments, the hearing device may be a hearing aid configured to compensate for a hearing loss of the user. The processing unit may be compensating for the hearing loss of the user. The hearing aid may be any type of a hearing aid, such as a behind the ear hearing aid, in the ear hearing aid, or the like. The hearing aid may be configured for binaural hearing. Having the hearing device of the present disclosure in the form of a hearing aid, additional functionalities of the hearing aid can be allowed, hearing problems of the user can be tracked, and an automatic control of the sound processing based on the hearing loss can be performed.

In some embodiments, the hearing device may be configured to receive a data signal comprising acoustic scene information. The processing unit may be configured to process the data signal and generate the decision based on the data signal. The data signal may be received from the user's smart phone and may give particulars about the scene the user is in. The data signal may comprise GPS information, a video of the acoustic scene, and a picture of the acoustic scene or at least a part of the environment the user is in. The data signal may further comprise a Wi-Fi signal related to the environment the user is in, a size of the room the user is in, a number of people in the room, a number of sources in the acoustic scene, etc. The audio signals received by microphones of the hearing device may have some information about the scene encoded therein. By receiving the data signal related to the acoustic scene the processing unit may reconstruct the objective acoustic scene with a high precision and thereby perform the decision with improved accuracy.

Also disclosed, in a second aspect, is a method performed by a hearing device. The hearing device is configured to be worn by a user. The user is in an environment defined by an acoustic scene. The hearing device comprises one or more microphones, a processing unit, a speaker, a wireless communication unit, and a stress evaluator. The method comprises receiving, at the one or more microphones, audio signals from acoustic sources in the environment. The method further comprises providing the received audio signals to the processing unit, the processing unit applying processing parameters to thereby process the audio signals and provide them to the speaker. The stress evaluator then measures stress parameters related to stress of the user which are then provided to the processing unit. The method further comprises generating an indication of stress of the user by the processing unit, stress of the user being related to the acoustic scene. The processing unit then decides whether to perform an action. The decision on whether to perform the action is based on the received audio signals and the indication of stress of the user.

The stress parameters may be the user's heart rate, body temperature, speech characteristics, skin resistance, etc.

In some embodiments, the action may comprise adjusting the processing parameters in the processing unit based on the decision. Adjusting the processing unit may comprise optimization of sound processing. An aim of adjusting the processing parameters may be to compensate for a hearing loss of the user and/or to compensate for stress of the user.

In some embodiments, the step of generating the indication of stress of the user may comprise detecting the user's speech, extracting the user's speech, and analysing the user's speech. The speech may be detected by the one or more microphones of the hearing device. The processing unit may then extract the speech from other undesired signals such as noise and further analyse it in order to generate the indication of stress of the user.

In some embodiments, the audio signals may comprise the user's speech.

In some embodiments, the action may comprise providing a request to the user to adjust the processing parameters based on the decision. The request may comprise suggestions for changing an operational mode, such as to change/use different listening features. The hearing device may communicate with the user's phone, send a message to the phone and then the user may switch between different operational modes.

In some embodiments, the method may further comprise the step of determining a complexity of the acoustic scene. The decision may further be based on the complexity of the acoustic scene. The complexity of the acoustic scene may be used in addition to the indication of stress in order to generate the decision. The complexity of the acoustic scene may be determined based on the received audio signals. The complexity of the acoustic scene may also be assessed by an external device combining multiple information sources, e.g. audio, vision, dynamics, etc. The complexity of the acoustic scene may be provided to the hearing device by, e.g., the user's smart phone, as it knows where the user is based on, e.g., GPS, Wi-Fi, etc.

The method according to the second aspect utilizes the hearing device according to the first aspect. The skilled person would therefore readily understand that any feature described in combination with the first aspect could also be combined with the second aspect, and vice versa. Accordingly, the remarks set forth above with reference to the first aspect are equally applicable on the second aspect.

The present disclosure relates to different aspects including the hearing device described above and in the following, and a corresponding method yielding to one or more of the benefits and advantages described in connection with the first mentioned aspect, and having one or more embodiments corresponding to the embodiments described in connection with the first mentioned aspect and/or disclosed in the appended claims.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1:
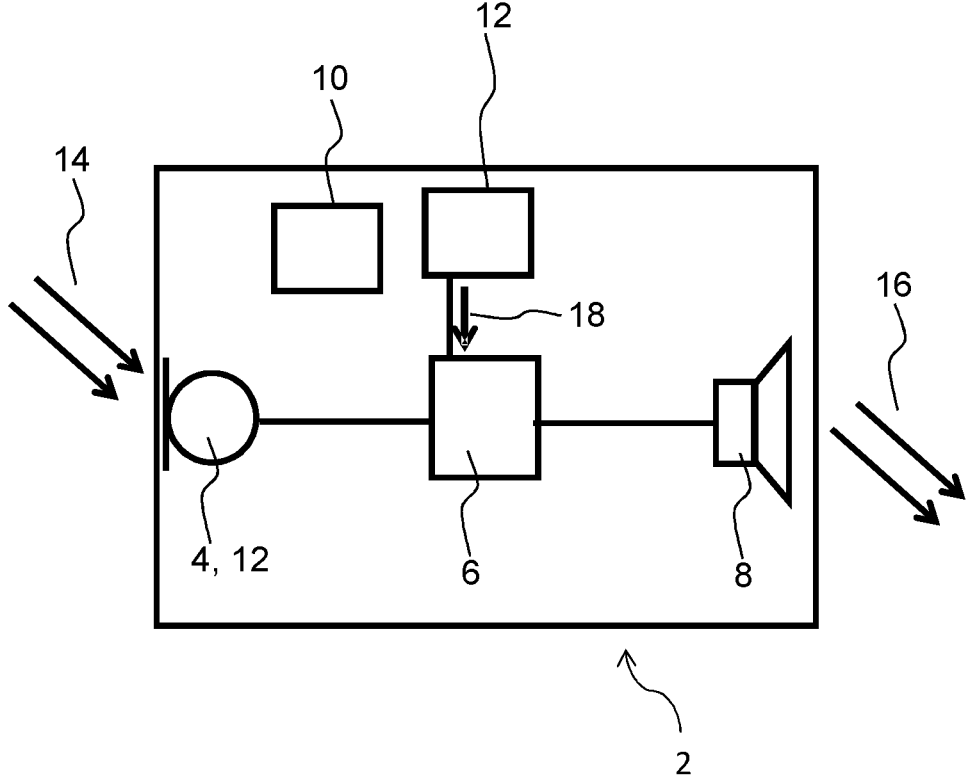
FIG. 1 schematically illustrates an exemplary hearing device.

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described. Throughout, the same reference numerals are used for identical or corresponding parts.

FIG. 1 schematically illustrates an exemplary hearing device 2. The hearing device 2 comprises a microphone 4, a processing unit 6, a speaker 8, a wireless communication unit 10, and a stress evaluator 12. The hearing device 2 may comprise more than one microphone 4. The microphone 4 is configured to receive audio signals 14 from audio sources in the environment and provide the audio signals 14 to the processing unit 6. The processing unit 6 is configured to apply processing parameters to thereby process the audio signals 14. The speaker 8 may be directly connected to the processing unit 6 and the processing unit 6 may provide the processed audio signal to the speaker 8. The speaker 8 may then convert the processed audio signal into a sound for the user, i.e. the speaker 8 is configured to provide the processed audio signals 16 to the user. The stress evaluator 12 is configured to generate an indication of stress 18 of the user. Stress of the user is related to the acoustic scene. The processing unit 6 is configured to decide whether to perform an action, the decision being based on the received audio signals 14 and the indication of stress 18 of the user. The stress evaluator 12 may comprise a temperature sensor, a skin resistance sensor, or similar. In some embodiments, the microphone 4 may serve the purpose of the stress evaluator 12.

Figure 2:
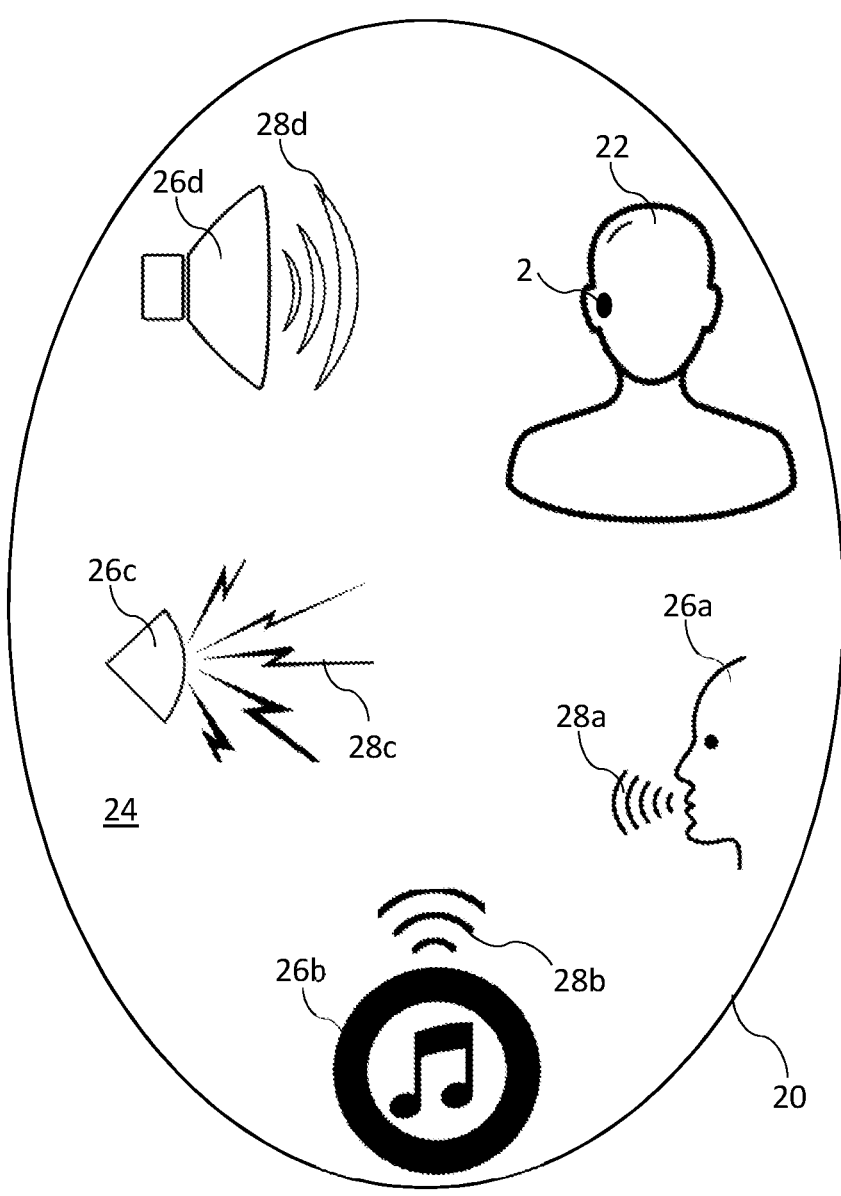
FIG. 2 schematically illustrates an exemplary environment with a user wearing a hearing device, FIG. 3 schematically illustrates an exemplary hearing device communicatively coupled to an external device, FIG. 4 schematically illustrates an exemplary method executed by the hearing device of FIG. 1, FIG. 5 schematically illustrates a hearing device which uses user's voice for stress evaluation

FIG. 2 schematically illustrates an exemplary environment 20 with a user 22 wearing a hearing device 2. The environment 20 is defined by an acoustic scene 24. The acoustic scene 24 comprises a plurality of audio sources 26, such as a person talking 26*a*, music source 26*b*, noise source 26*c*, loudspeaker 26*d*. Each of the audio sources 26*a*, 26*b*, 26*c*, and 26*d* generates a corresponding audio signal 28*a*, 28*b*, 28*c*, and 28*d*. The environment 20 may also comprise a plurality of visual sources which contribute to the user's cognitive load, attention, and therefore stress. Some of the audio sources, e.g. the person talking 26*a* and the loudspeaker 26*d* at the same time represent the visual sources as the user 22 may make notice of them while being in the environment. The arrangement of the audio sources 26*a*, 26*b*, 26*c*, and 26*d* may also affect the user's stress. For instance, if the noise source 26*c* is in a close proximity of the user 22, the user's stress level may be increased compared to the situation if the noise source 26*c* was far away. The hearing device 2 receives the audio signals 28*a*, 28*b*, 28*c*, and 28*d* via the one or more microphones (not shown). The audio signals 28*a*, 28*b*, 28*c*, and 28*d* are then processed by the processing unit of the hearing device 2. The processing unit may reconstruct the acoustic scene 24 and determine its complexity based on the received audio signals 28*a*, 28*b*, 28*c*, and 28*d* from the received acoustic signals 28*a*, 28*b*, 28*c*, and 28*d*, the processing unit may predict whether the user 22 is expected to be stressed or not. Alternatively, the processing unit of the hearing device 2 may estimate a stress level of the user 22 given the acoustic scene 24. This estimate may then be compared with the stress evaluator output, i.e. the indication of stress, to finally decide on whether to perform an action.

Figure 3:
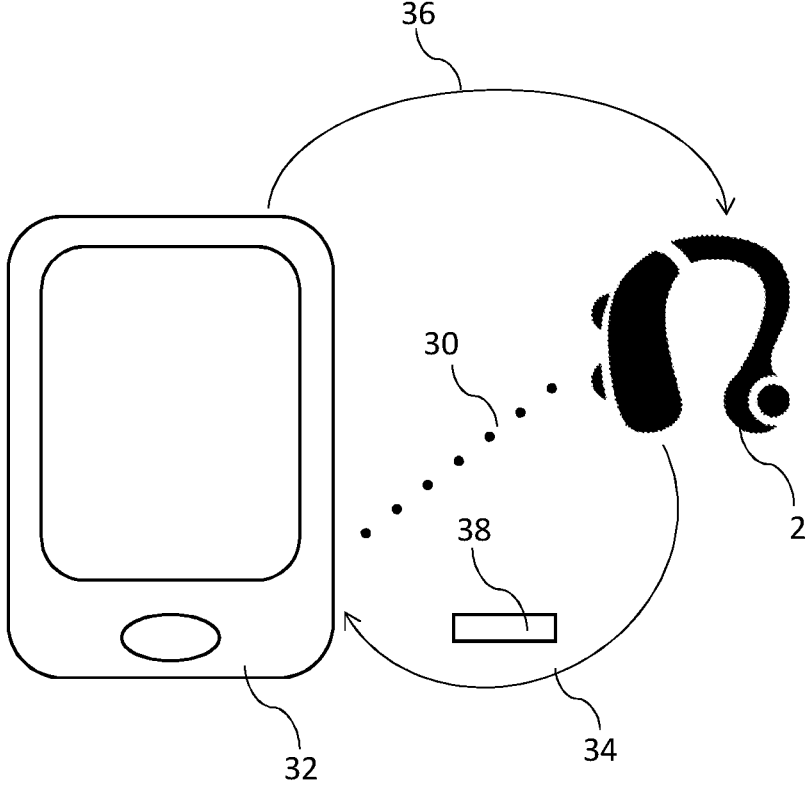

FIG. 3 schematically illustrates an exemplary hearing device 2 communicatively coupled to an external device 32. The communication link 30 may be a wireless link or it may be a wired connection. The external device 32 may be the user's smart phone, the user's computer, a server being a part of cloud, etc. The hearing device 2 may simultaneously be connected with more than one external device 32. The hearing device 2 may send data to the external device 32 through a first communication channel 34. The data sent from the hearing device 2 may include packages 38 comprising received audio signals and corresponding measurements from the stress evaluator. The packages 38 may therefore relate to users' perceptual hearing for a given environment. These data may be used for building up a database with historical data in the external device 32. The external device 32 may communicate with other hearing devices used by other users (not shown) which can then further contribute to the database and historical data. The external device 32 may then send these historical data to the hearing device 2 through another communication channel 36. The processing unit may then generate the decision based on the historical data. In one embodiment, the hearing device 2 may detect/identify the user's speech and forward it to the external device 32 for processing and/or analysis. The external device 32 may then send back the analysis of the speech which may be used by the processing unit in determination of the indication of stress.

Figure 4:
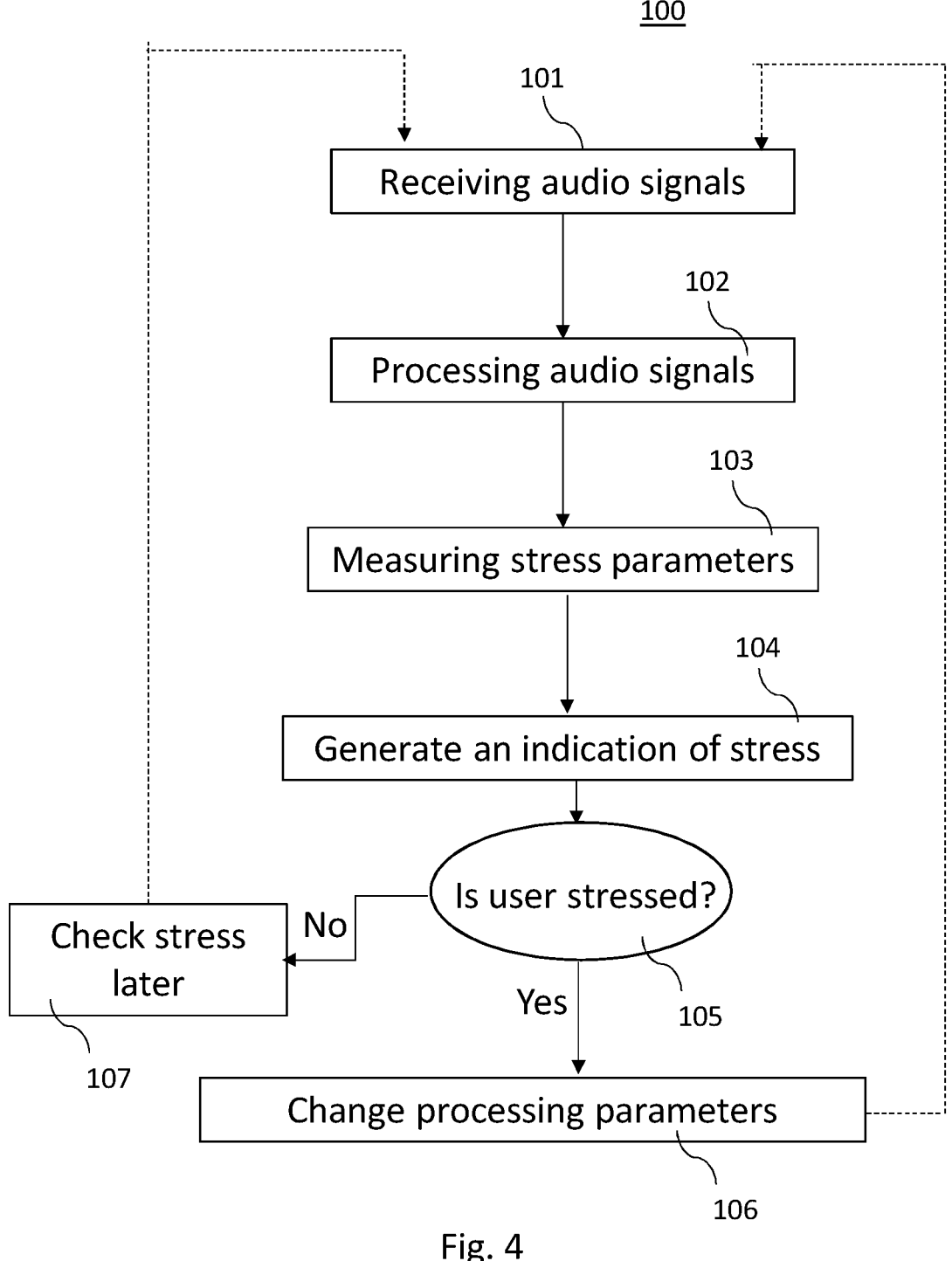

FIG. 4 schematically illustrates an exemplary method 100 executed by the hearing device shown on FIG. 1. The method comprises receiving 101 audio signals at the one or more microphones of the hearing device. The audio signals originate from the acoustic sources arranged in the environment. The method further comprises providing the received audio signals to the processing unit (not shown). The processing unit then applies processing parameters to thereby process 102 the audio signals and provide them to the speaker. The stress evaluator then measures 103 stress parameters related to stress of the user which are then provided to the processing unit. The method further comprises generating 104 an indication of stress of the user by the processing unit, stress of the user being related to the acoustic scene. The processing unit then decides whether to perform an action. The decision on whether to perform the action is based on the received audio signals and the indication of stress of the user. The decision about performing and action may be based on a predetermined criteria, i.e. the indication of stress and the received audio signals may be compared 105 with the predetermined criteria and the result of the comparison may be that the user is not stressed. The processing unit may then check later again 107 whether the user is stressed, by performing the same steps again. If the outcome of the comparison is positive, i.e. the user is stressed, the processing unit may change 106 the processing parameters in order to reduce the stress. After the processing parameters are changed the method 100 may be performed again in order to check whether the change in the processing parameters resulted in reduction of stress. If stress is reduced but the user is still stressed the processing parameters may be changed further. If stress of the user is increased the processing parameters may need to be reset to previous values.

Figure 5:
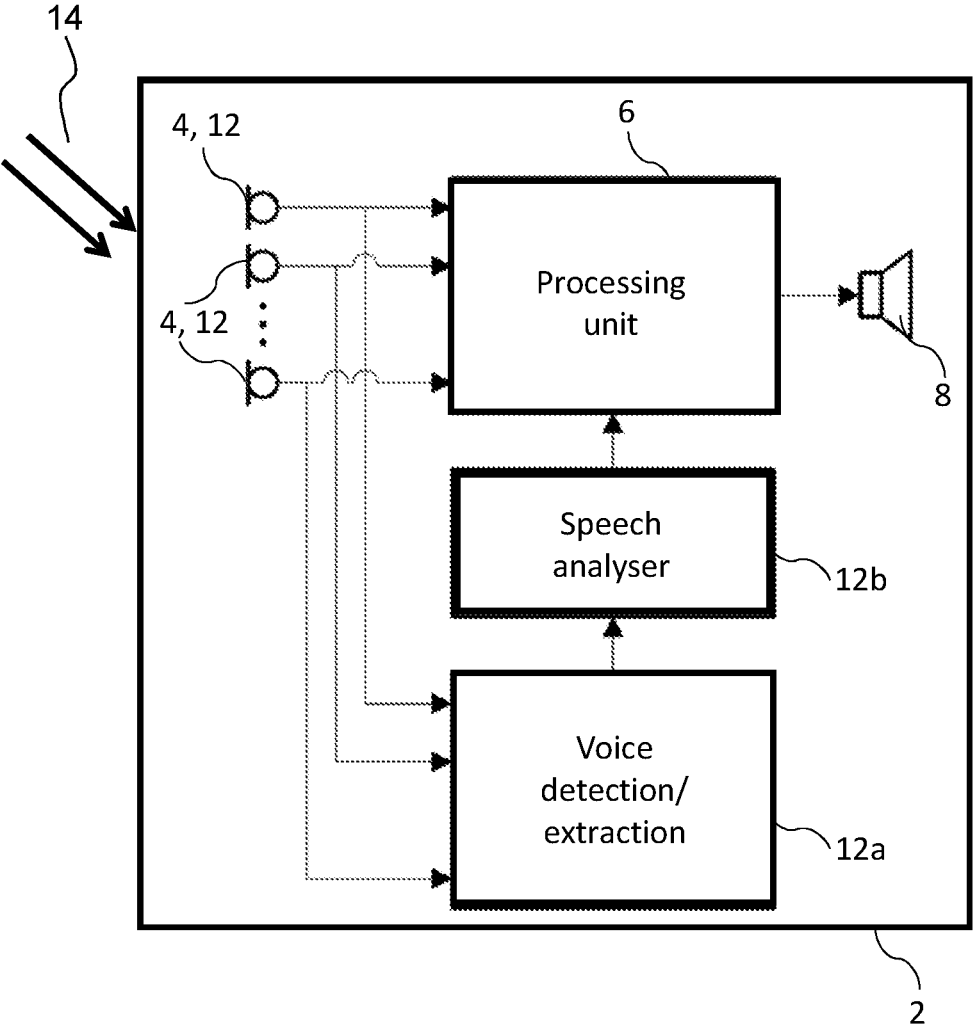

FIG. 5 schematically illustrates a hearing device 2 using the user's voice for stress evaluation. One or more microphones 4 of the hearing device 2 is configured to detect various acoustic signals from the environment and send these to the processing unit 6. The processing unit applies processing parameters to the received audio signals and outputs processed audio signals to the speaker 8. In this embodiment, the microphones 4 also detect the user's voice, thereby serving as a part of a stress evaluator 12. The microphones 4 also send the audio signals to a signal processor 12a forming part of the stress evaluator 12. The signal processor is configured to detect and extract the user's voice from the received audio signals 14. The extracted user's voice is sent to a speech analyser 12b also forming part of the stress evaluator 12. The speech analyser 12b is configured to determine the indication of stress and send it to the processing unit 6. The processing unit 6 then, based on the indication of stress obtained from the stress evaluator 12 and the received audio signals 14, decides whether to perform an action, such as changing the processing parameters.

Figure 6:
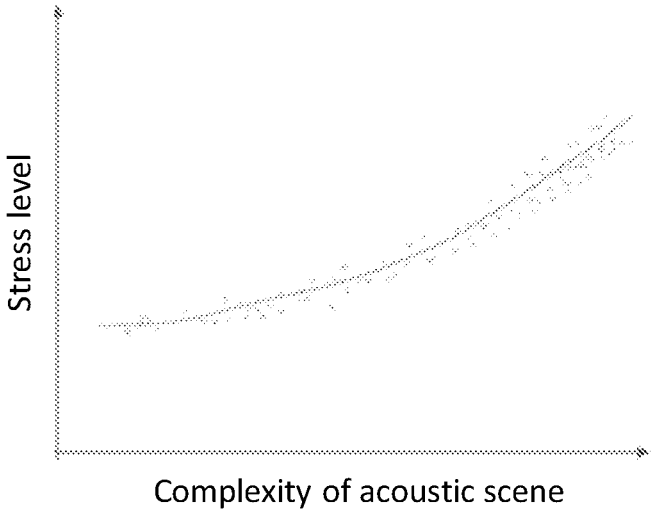
FIG. 6 illustrates dependency of a stress level and a complexity of an acoustic scene.

FIG. 6 illustrates dependency of a stress level (y-axis) and a complexity of an acoustic scene (x-axis). From the graph it can be seen that the more complex the acoustic scene is, the stress level will be higher. Such dependency may form part of historical data. The historical data may define expected stress parameter. The expected stress parameter may depend on the complexity of the acoustic scene.

Figure 7:
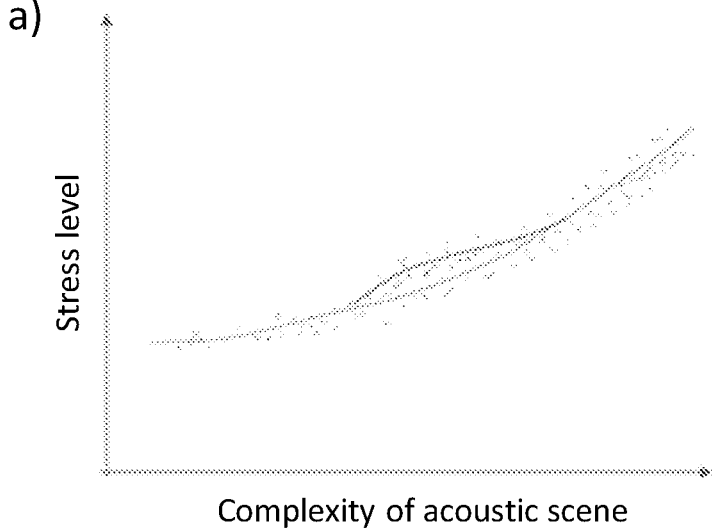
FIGS. 7*a* and 7*b* illustrate a detection of an uncompensated hearing loss.
Figure 7:
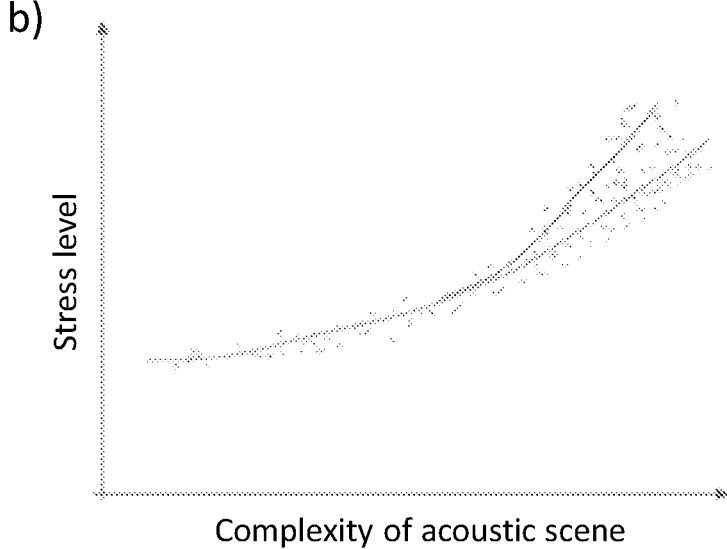

FIGS. 7a) and 7b) illustrate a detection of an uncompensated hearing loss. The graph in FIGS. 7a) and 7b) shows dependency of the stress level (y-axis) on the complexity of an acoustic scene (x-axis). The regular (brighter) curve shows historical data generated over time based on the user's previous experience or based on other users with similar profile. The irregular (darker) curve shows actual stress level measured by the stress evaluator. The irregular (darker) curve shows that the user starts to show higher stress relative to the historical average of acoustic scenes with similar complexity. Such behaviour may be the sign of an uncompensated hearing loss.

Although particular features have been shown and described, it will be understood that they are not intended to limit the claimed invention, and it will be made obvious to those skilled in the art that various changes and modifications may be made without departing from the scope of the claimed invention. The specification and drawings are, accordingly to be regarded in an illustrative rather than restrictive sense. The claimed invention is intended to cover all alternatives, modifications and equivalents.

14

LIST OF REFERENCES

2 hearing device
4 microphone
6 processing unit
8 speaker
10 wireless communication unit
12 stress evaluator
14 audio signals
16 processed audio signals
18 indication of stress
20 environment
22 user
24 acoustic scene
26 audio sources
28 audio signals
30 communication link
32 external device
34 first communication channel
36 second communication channel
38 package
100 method executed by the hearing device
101 method step of receiving audio signals
102 method step of processing audio signals
103 method step of measuring stress parameters
104 method step of generating an indication of stress
105 method step of determining whether the user is stressed?
106 method step of changing processing parameters
107 method step of checking stress later

The invention claimed is:

1. A hearing device configured to be worn by a user in an environment, the hearing device comprising:
   a processing unit configured to apply a processing parameter of the hearing device to process audio signals, the audio signals comprising microphone signals;
   a speaker configured to provide sound to the user based on the processed audio signals; and
   a wireless communication unit;
   wherein the processing unit is configured to obtain a stress parameter relating to a stress of the user;
   wherein the processing unit is configured to determine whether a hearing-loss of the user is uncompensated based on a difference between the stress parameter and an expected stress parameter; and
   wherein the expected stress parameter is variable based on a complexity of an acoustic scene.

2. The hearing device according to claim 1, further comprising a temperature sensor, a heart rate sensor, a skin resistance sensor, or any combination of the foregoing, for providing the stress parameter.

3. The hearing device according to claim 1, further comprising one or more microphones configured to provide the stress parameter.

4. The hearing device according to claim 3, wherein the one or more microphones are configured to receive sound in the environment, and provide the audio signals.

5. The hearing device according to claim 1, wherein the hearing device is configured to generate an indication of stress, the indication of stress being based on the stress parameter.

6. The hearing device according to claim 1, wherein the hearing device is configured to generate an indication of stress, the indication of stress being based on at least a speech of the user.

7. The hearing device according to claim 1, wherein the processing unit is configured to change the processing parameter based on a change in an acoustic scene.

8. The hearing device according to claim 1, wherein the hearing device is configured to forward speech data indicating a speech of the user to an external device.

9. The hearing device according to claim 1, wherein the hearing device is communicatively coupled to a database comprising historical data, the historical data relating to a perceptual hearing of the user and/or a general perceptual hearing, wherein the hearing device is configured to generate an indication of stress based on the historical data.

10. The hearing device according to claim 1, wherein the processing unit is configured to determine whether the hearing-loss of the user is uncompensated based also on an acoustic scene.

11. The hearing device according to claim 1, wherein the hearing device is a hearing aid configured to compensate for a hearing loss of the user.

12. The hearing device according to claim 1, wherein the hearing device is configured to receive a data signal comprising acoustic scene information, the processing unit being configured to process the data signal, and based on the data signal, determine whether to perform an action.

13. The hearing device according to claim 1, wherein the hearing device is configured to generate an indication of stress based on the stress parameter; and wherein the processing unit is configured to decide, based indirectly on the stress parameter, whether to perform an action, by making a decision based on the indication of stress.

14. A method performed by a hearing device, the hearing device being configured to be worn by a user in an environment, the hearing device comprising a processing unit, a speaker, and a wireless communication unit, the method comprising:

receiving, by the processing unit, audio signals, the audio signals comprising microphone signals;

applying, by the processing unit, a processing parameter of the hearing device to process the audio signals; and obtaining a stress parameter indicating a stress of the user;

wherein the method further comprises determining whether a hearing-loss of the user is uncompensated based on a difference between the stress parameter and an expected stress parameter; and wherein the expected stress parameter is variable based on a complexity of an acoustic scene.

15. The method according to claim 14, further comprising generating an indication of the stress of the user based on the stress parameter and a speech analysis.

16. The method according to claim 14, further comprising determining a complexity of the acoustic scene, wherein the expected stress parameter is based on the complexity of the acoustic scene.

17. The hearing device according to claim 1, wherein the hearing device is configured to determine an indication of stress based on the stress parameter, and to transmit the indication of stress to an external device via the wireless communication unit of the hearing device.

18. The hearing device according to claim 17, wherein the processing unit is configured to adjust the processing parameter after the indication of stress is generated by the hearing device.

19. A hearing device configured to be worn by a user in an environment, the hearing device comprising:

a processing unit configured to apply a processing parameter of the hearing device to process audio signals;

a speaker configured to provide sound to the user based on the processed audio signals; and a wireless communication unit;

wherein the hearing device comprises a non-audio sensor configured to provide a non-audio sensor output as a stress parameter, wherein the hearing device is configured to process the non-audio sensor output the non-audio sensor output indicative of a mental stress of the user, and wherein the hearing device is configured to determine whether a hearing-loss of the user is uncompensated based on a difference between the stress parameter and an expected stress parameter; and wherein the expected stress parameter is variable based on a complexity of an acoustic scene.

20. The hearing device according to claim 19, wherein the hearing device is configured to transmit speech signal to an external device, and receive a processed speech signal from the external device.

21. The hearing device according to claim 19, wherein the processing unit is configured to decide, whether to perform an action based on the stress parameter.

22. The hearing device according to claim 19, wherein hearing device is configured to determine a stress indicator based on the stress parameter, and to transmit the stress indicator to a phone via the wireless communication unit of the hearing device.

23. The hearing device according to claim 19, wherein hearing device is configured to determine a stress indicator based on the stress parameter, and to transmit the stress indicator to a server via the wireless communication unit of the hearing device.

24. The hearing device according to claim 19, wherein the hearing device is configured to inform the user regarding the mental stress of the user.

25. The hearing device according to claim 19, wherein the hearing device is configured to cause a suggestion to change the processing parameter of the hearing device to be provided to the user based on the stress parameter, wherein the suggestion allows the user to have freedom to decide whether to change the processing parameter of the hearing device.

26. The hearing device according to claim 19, wherein the hearing device is configured to compare a level of stress indicated by the non-audio sensor output with a threshold stress value.

27. The hearing device according to claim 1, wherein the hearing device is configured to cause a suggestion to change the processing parameter to be provided to the user, wherein the suggestion is based on the stress parameter and allows the user to have freedom to decide whether to change the processing parameter of the hearing device.

28. The hearing device according to claim 1, wherein the stress parameter comprises a non-audio sensor output.

29. The hearing device according to claim 1, wherein the stress parameter comprises speech information derived from the audio signals.

30. The method according to claim 14, further comprising causing a suggestion to change the processing parameter to be provided to the user, wherein the suggestion is based on the stress parameter and allows the user to have freedom to decide whether to change the processing parameter of the hearing device.

31. The hearing device according to claim 1, wherein the expected stress parameter is based on historical data.

32. The method according to claim 14, wherein the expected stress parameter is based on historical data.

33. The hearing device according to claim 19, wherein the expected stress parameter is based on historical data.

\* \* \* \* \*